United States Patent [19]

Dufresne et al.

[11] Patent Number: 4,699,143
[45] Date of Patent: Oct. 13, 1987

[54] ELECTRICAL SIMULATOR FOR BIOLOGICAL TISSUE HAVING REMOTE CONTROL

[75] Inventors: Joel R. Dufresne; Alan P. Dieken, both of St. Paul, Minn.

[73] Assignee: Minnesota Mining and Manufacturing Company, St. Paul, Minn.

[21] Appl. No.: 745,071

[22] Filed: Jun. 17, 1985

[51] Int. Cl.⁴ ............................................. A61N 1/36
[52] U.S. Cl. ............................................. 128/419 R
[58] Field of Search ................ 128/419 PG, 421–422, 128/419 C, 419 E, 423

[56] References Cited

U.S. PATENT DOCUMENTS

| | | | |
|---|---|---|---|
| 4,243,043 | 1/1981 | Sevastianov et al. ............... | 128/422 |
| 4,255,790 | 3/1981 | Hondeghem ........................ | 128/421 |
| 4,424,812 | 1/1984 | Lesnick ........................ | 128/419 PG |
| 4,431,000 | 2/1984 | Butler et al. . | |
| 4,431,002 | 2/1984 | Maurer et al. . | |
| 4,440,173 | 4/1984 | Hudziak et al. .............. | 128/419 PG |
| 4,476,869 | 10/1984 | Bihn . | |
| 4,528,984 | 7/1985 | Morawetz et al. ................. | 128/421 |
| 4,539,993 | 9/1985 | Stanton ............................... | 128/421 |

Primary Examiner—William E. Kamm
Attorney, Agent, or Firm—Donald M. Sell; James A. Smith; William D. Bauer

[57] ABSTRACT

An electrical stimulator for biological tissue having remote control. A remote element communicates an operator response to the electrical stimulator. A control element samples the communication from the remote element and adjusts one or more of certain of sets of stimulus parameters maintained in a storage element and utilizes the adjusted stimulus parameters to generate an electrical stimulus signal or utilizes the communciation from the remote element to trigger the generation of an electrical stimulus signal based upon the stored stimulus parameters.

1 Claim, 4 Drawing Figures

ELECTRICAL SIMULATOR FOR BIOLOGICAL TISSUE HAVING REMOTE CONTROL

BACKGROUND OF THE INVENTION

The present invention relates generally to electrical stimulators for biological tissue and more particularly to electrical stimulators for having remote control.

Electrical stimulators providing an electrical stimulus signal are useful for biological tissue. One significant use for electrical stimulators of this type is for transcutaneous electrical nerve stimulation (TENS) which generate carefully controlled electrical stimulus signals which are delivered via suitable electrodes through a patients' skin to underlying biological tissue. The electrical stimulus signals are utilized masking pain signals, for example, the sensation of pain felt by a patient after surgery. Because the patient's response to transcutaneous electrical nerve stimulation (TENS) very significantly, a wide range of electrical stimulus signals must be provided. A second use of electrical stimulators is for neuromuscular stimulation (NMS) in order to initiate or control muscular contraction in a patient. Since a wide variety of muscular actions are available again a wide variety of electrical stimulus signals must be provided.

Electrical stimulators may deliver electrical stimulus signals which may be a pulsatile signal. Such pulsatile signals can originate from differing modes of operation of the electrical stimulator.

In a transcutaneous electrical nerve stimulation (TENS) mode, electrical stimulators deliver an electrical stimulus signal which is pulsatile according to pre-determined stimulus parameters such as pulse amplitude, pulse duration and pulse frequency or repetition rate. While such stimulus parameters typically may be predetermined or specified as, for example, from an external programmer, patient (user) response to such parameters can vary significantly. Thus, it is desirable to vary, or alter such stimulus parameters on a real-time basis so that the electrical stimulus signal generated may be adjusted to the individual patients' needs and comfort.

In a neuromuscular stimulation (NMS) mode, an electrical stimulator may deliver an electrical stimulus signal consisting of a pulse train with a predetermined sequence of stimulation parameters such as pulse amplitude, pulse duration and pulse frequency or repetition rate. While the pulse train may be specified by predetermined stimulus parameters, it is desirable to have the timing of the application of such a pulse train in the electrical stimulus signal under real-time user (patient) control.

SUMMARY OF THE INVENTION

Thus, it is desirable to have an electrical stimulator able to produce an electrical stimulus signal with stimulus parameters or timing of application of the stimulus parameters under real-time remote control from the user (patient).

The present invention provides an electrical stimulator of biological tissue having a storage element for storing a plurality of sets of stimulus parameters. A converting element is provided for converting a selected one of the plurality of sets of stimulus parameters to an electrical stimulus output signal which is adapted to be supplied to the biological tissue. A remote element is provided for communicating an operator or user response to the electrical stimulator. A control element is operatively coupled to the storage element, to the converting element and to the remote element. The control element is responsible for selecting and coupling one of the plurality of sets of stimulus parameters from the storage element to the converting element, for varying the value of at least one of the stimulus parameters of the one of the plurality of sets of stimulus parameters selected, with the selecting, varying and coupling being a function of the remote element under user control. In a preferred embodiment, the remote element may be used to change at least one of the stimulus parameters related to timing, pulse amplitude, pulse duration and pulse frequency or repetition rate. In another preferred embodiment of the present invention, the electrical stimulator is useful for neuromuscular stimulation (NMS) and for transcutaneous electrical nerve stimulation (TENS). The remote means has switches which are used to supply trigger information when the electrical stimulator is providing NMS and for stimulus parameter value control when the electrical stimulator is providing TENS.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
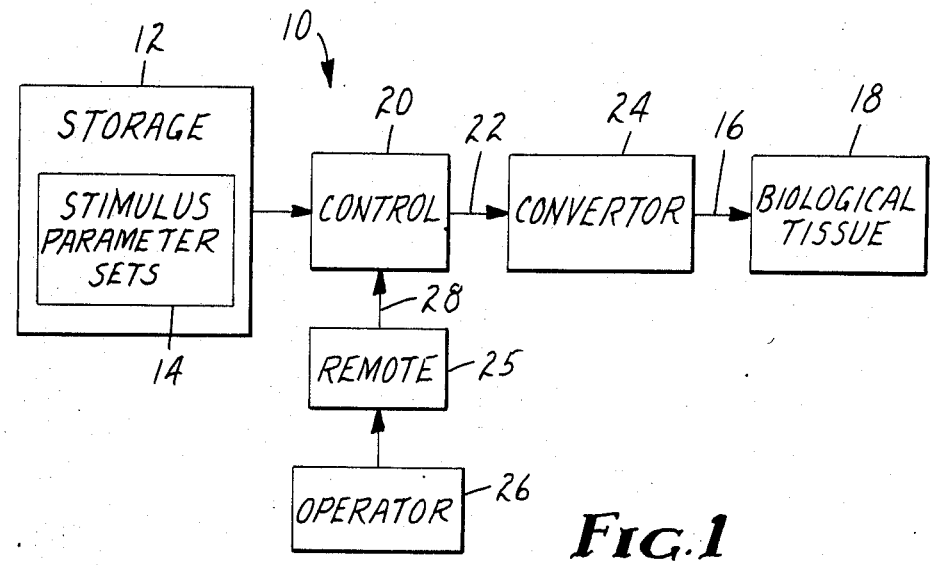
FIG. 1 is a block diagram of an electrical stimulator of the present invention.

FIG. 1 is a block diagram of an electrical stimulator 10 according to the present invention. Storage element 12 provides storage for a plurality of sets of stimulus parameters 14 which can be used by the electrical stimulator 10 to generate an electrical stimulus signal 16 to be applied to the biological tissue 18. The sets of stimulus parameters 14 may be used to specify an electrical stimulus signal 16 which may be utilized in transcutaneous electrical nerve stimulation (TENS) or for neuromuscular stimulation (NMS) depending upon the operational mode of the electrical stimulator 10. It is expected and anticipated that the sets of stimulus parameters 14 are stored within storage element 12 from an external programming device. It is expected and anticipated that storage element 12 is a digital storage element such as a digital memory device to digitally store sets of stimulus parameters 14. Control element 20 selects at least one of the sets of stimulus parameters 14 from the storage element 12 and generates a series or a sequence of digital output words 22 which is supplied to converter 24. Converter 24 converts each of the digital output words 22 into an electrical stimulus signal 16 having certain voltage and current characteristics with the presentation of a series of digital output words 22. Converter 24 produces a series of voltages and currents to produce an electrical stimulus signal 16 which depends upon the content of the sequence of digital output words 22. The electrical stimulus signal generated thus may be pulsatile, as in a preferred embodiment, or may replicate an analog signal. Remote element 25 is provided under operator 26 (which can be a user or patient) control to provide signals 28 to control element 20. Remote element 25 may thus be used to send signals 28 to the control element 20 in order to change or adjust the stimulus parameters 14 contained in storage element 12, to vary or modulate the digital output words 22 produced by the control element 20 in response to the sets of stimulus parameters 14 obtained from storage element 12 or to provide trigger information to control element 20 to specify the timing of application of digital output words 22 so that an electrical stimulus signal 16 may be generated under remote control by the operator 26.

Figure 2:
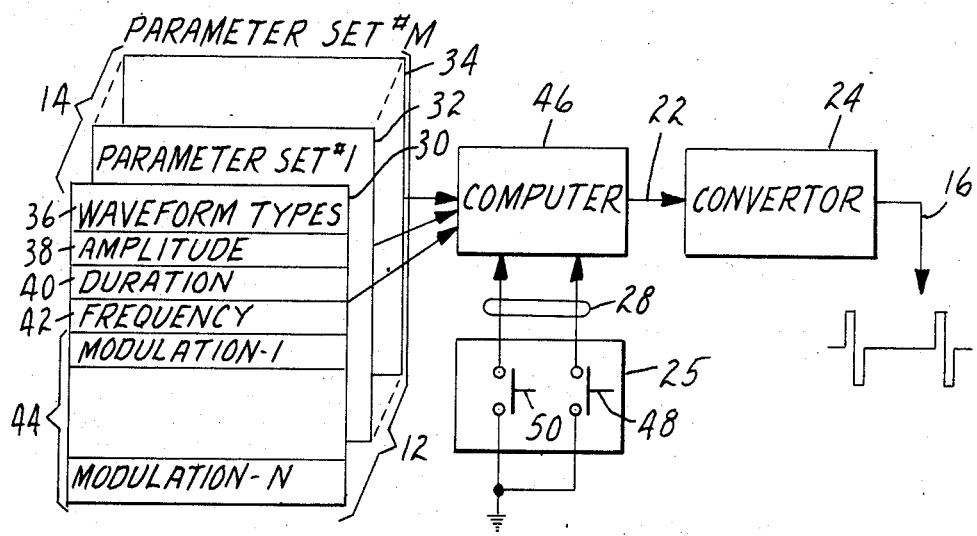
FIG. 2 is illustrative of one implementation of an electrical stimulator of FIG. 1.

Operation of the electrical stimulator 10 of the present invention may be understood in more detail by referencing to FIG. 2. The storage element 12 is represented as diagramatically containing a plurality of sets of stimulus parameters 14, namely, stimulus parameter set 1 (30), stimulus parameter set 2 (32) and stimulus parameter set M (34). Each of the stimulus parameter sets (30, 32 and 34) contain information designed to define to the control element 20 the digital output words 22 which may be generated so that a proper and distinct electrical stimulus signal 16 may be generated by converter 24. An example of the types of information contained within the stimulus parameter set is illustrated by parameter set 1 (30) in which is specified waveform type 36, pulse amplitude 38, pulse duration 40, pulse frequency or repetition rate 42 and modulation factors 44. Waveform type 36 may specify that an analog or pulsatile signal may be generated or the type of pulsatile signal as unipolar or bipolar. Pulse amplitude 38 may specify a predetermined maximum or mean value of the amplitude of the electrical stimulus signal 16 to be generated and in a preferred embodiment specifies the maximum value of pulse amplitude. Pulse duration 40 in a pulsatile signal may be used to specify the nominal value of pulse width or in a preferred embodiment specify the maximum value of pulse width. Pulse frequency 42 may be used to specify the frequency with which the pulsatile pulses are generated in the electrical stimulus signal 16 or, put another way, the repetition rate of the pulses contained within the electrical stimulus signal 16. Modulation factors 44 may be utilized by control element 20 to specify that the electrical stimulus signal 16 may be modulated according to some predetermined algorithm specified by the modulation factors 44 or that one or more of the stimulus parameters 14 may be modulated on a random basis. In the preferred embodiment illustrated in FIG. 2, storage element 12 may be represented by digital storage means such as a randomly addressable memory (RAM) of a size and configuration necessary to store the plurality of sets of stimulus parameters 14. Control element 20 in FIG. 2 is accomplished by computer 46. In general, computer 46 may be any of a number of computers or microprocessors of a general purpose to accomplish the generation of the digital output words 22. In particular, in a preferred embodiment computer 46 is a model 80C49 microprocessor manufactured by Intel Corporation. Computer 46 accesses storage element 12 to retrieve the sets of stimulus parameters 14. Remote element 25 is coupled to computer 46 to provide the operator control necessary to vary, adjust or trigger the generation of the digital output words 22 by the computer 46. In a preferred embodiment, remote element 25 produces two discrete signals 28 to be supplied to computer 46. The generation of signals 28 is under a remote operator control and is illustrated in FIG. 2 as being switch elements 48 and 50. Converter 24 takes a sequence of digital output words 22 and converts them to an electrical stimulus signal 16. It is preferred that converter element 24 is a digital-to-analog converter which receives digital output words 22 provides an accurate conversion to an electrical stimulus signal 16. In a preferred embodiment, the converter 24 is a linear current output circuit as is described in copending U.S. patent application filed by Joel F. Dufresne and Alan P. Dieken, entitled, "Electrical Stimulator For Biological Tissue Utilizing Linear Current Output Circuit", filed the same day as the present application, identified as File Number 40008USA1A and assigned to the assignee of the present application, the contents of which are hereby incorporated by reference.

Figure 3A:
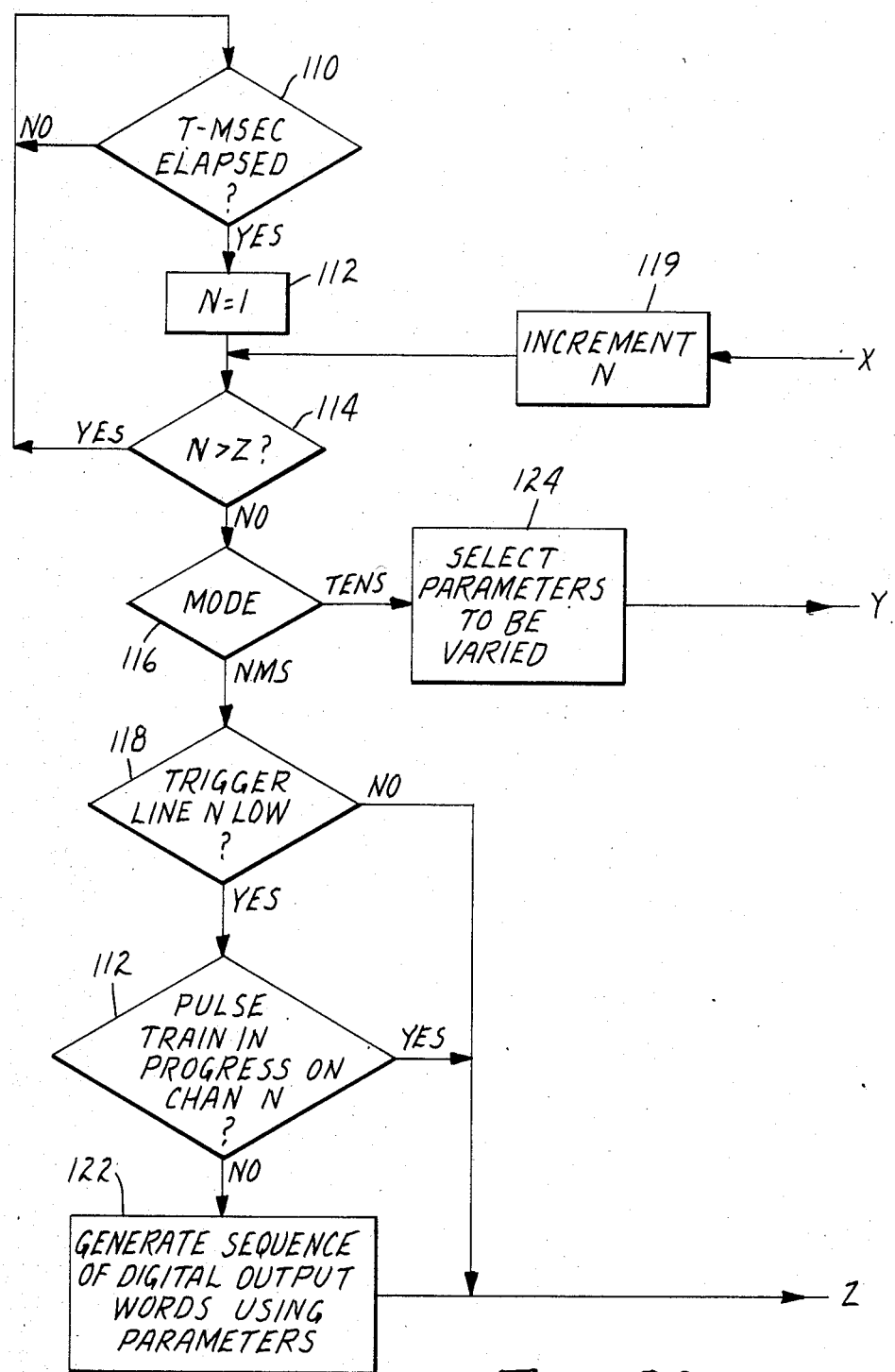
FIGS. 3A and 3B illustrate a flow diagram of a software program to control the computer in FIG. 2.
Figure 3B:
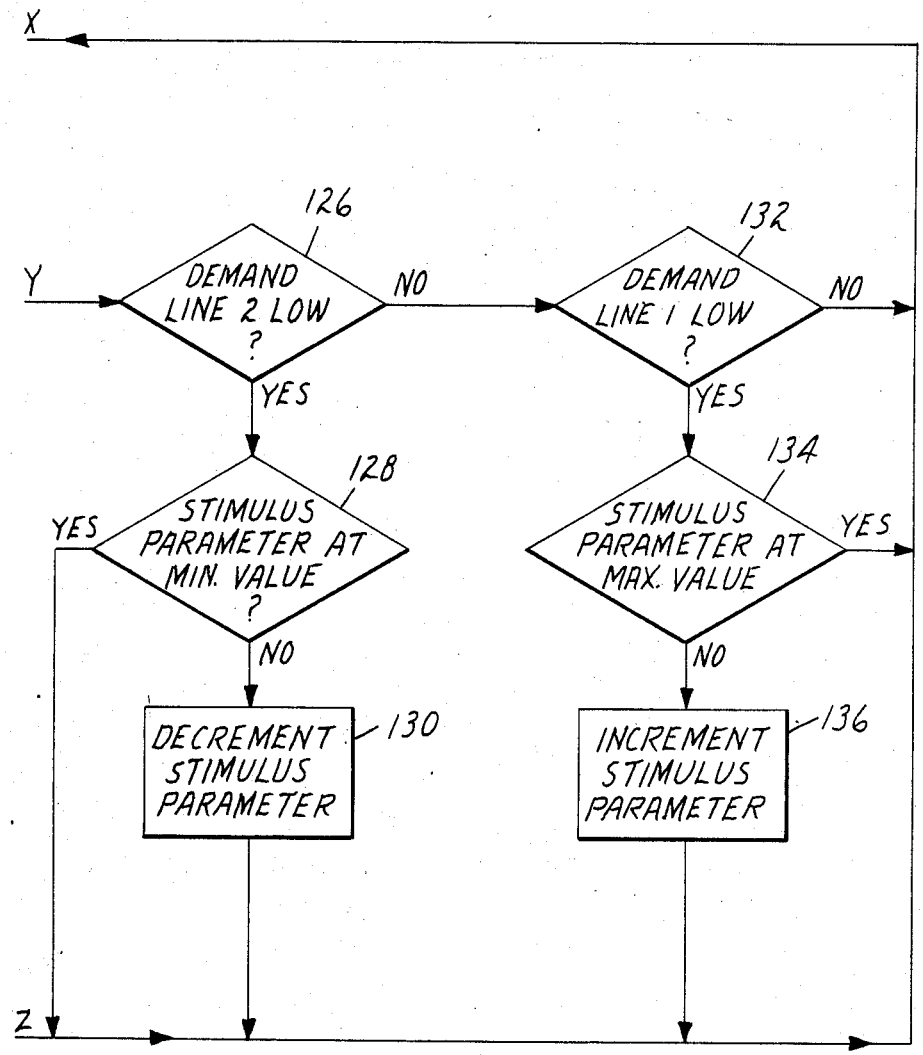

Operation of computer 46 can be more readily understood by reference to the flow chart of FIG. 3 which represents the steps of computer program may be utilized by a computer 46. A program constructed according to the flow chart of FIG. 3 will implement the dual functionality of remote element 24 in conjunction with the features of the present invention. The program begins by periodically sampling signals 28 to see if a response has been submitted by remote element 24. This is represented by block 110 which inquires to whether a predetermined amount of time has elapsed. In a preferred embodiment, the program waits or counts until 100 milliseconds have elapsed before preceding to block 112 which sets the value of N=1. Setting the value of N equal to one specifies that, for a multichannel electrical stimulator 10 the program will first proceed the sample for channel number one. The program then passes through decision block 112 which inquires if N is greater than 2. For a two channel electrical stimulator 10 illustrated by this program, an N greater than two means that both channels have already been sampled. Since N has just been set to 1 in block 112, the program passes to decision block 116 which branches depending upon the mode of operation of the electrical stimulator 10. The mode of operation of electrical stimulator 10 may be set under program control or may be set by an external switch (not illustrated). The branch at block 116 represents the beginning of the dual functionality of the remote element 24 of the electrical stimulator 10. If the electrical stimulator 10 is in neuromuscular stimulation (NMS) mode, the program passes to block 118 which samples one or more of signals 28 from remote element 24. If there is no active response on signals 28 from remote element 24, the program increments N by one returns to element 114. If there is a response on the appropriate signal line 28 from remote element 24, the program then moves to block 120 which checks to see if there is currently an electrical stimulus signal, or a pulse train for NMS, in progress on the channel under consideration in this case channel 1. If a pulse train is in progress, the computer program again returns to block 114 via block 119 which increments N. The process may be repeated on the next channel of the electrical stimulator 10. However, if no pulse train is currently in process on the channel under consideration, the conditions are right and the computer program enables the generation of a sequence of digital output words at block 122 according to the set of stimulus parameters 14 contained within storage element 12. After a fixed period of time, the generation of digital ouput words is disabled. Also, in general, there are other conditions in which an electrical stimulator 10 would enable the generation of digital output words. Following the generation or the commencement of the generation of the sequence of digital output words 22, program returns to block 114 after incrementing N at block 119 so that that process may be repeated on the next channel.

If at block 116, however, the mode of the electrical stimulator 10 is in transcutaneous electrical nerve stimulation (TENS) mode, the remote element 24 may be used to vary one or more of the stimulus parameters 14 according to the response of one or more of signal lines 28. In this case, the program at block 124, selects the parameter or parameters which may be varied according to the alogrithm illustrated in FIG. 3. It is to be understood, of course, that if more than one of the stimulus parameters 14 are to be varied, the computer program may independently vary each parameter by repeating that portion of the flow chart for the variation of parameters for each of the stimulus parameters 14 to be varied. After selecting the particular parameter to be varied at block 124, the program then samples the first of the signals 28 to see if it is active at block 126. This is illustrated by the question "demand line 2 low? "Demand line two is one of the signal lines 28 and may be made low, or active, upon the activation of one of the switch elements, as for example, switch element 50. If demand line 2 is active, indicating a response from remote element 24 requesting a reduction in the selected stimulus parameter, for example, pulse amplitude, the program at block 128 inquires as to whether that particular stimulus paramter is already at its minimum allowed value. The minimum allowed value of the stimulus parameter may be one of the conditions set forth in the modulation parameters 44. If the stimulus parameter is already at its minimum value, it can not be decremented further and the program returns to block 114 after incrementing the channel number N at block 119. If the stimulus parameter is not at its minimum value, the program at block 130 decrements the stimulus parameter, for example, pulse amplitude, and returns to block 114 after incrementing channel number N at block 119. If demand line 2 is not active at block 126, the program then samples demand line 1 at block 132. Demand line 1 being low or active is one of the signal lines 28 which may be activated by one of the switch elements, as for example, switch element 48 of remote element 24. Demand line 1 being active would be used to indicate a desire to increase the value of the selected stimulus parameter. The program then inquires at block 134 whether that selected stimulus parameter, for example, pulse amplitude, is already at its maximum value. The maximum value of the stimulus parameter may be that value specified in parameter set 14, as for example, pulse amplitude 48 or may be specified in one of the modulation factors 44. If a stimulus parameter is already at its maximum value it can not be incremented and the program returns to block 114 after incrementing the channel number N at block 119. If the selected stimulus parameter, for example, pulse amplitude, is not at its maximum value the program increments the selected stimulus parameter, for example, pulse amplitude at block 136. Program then returns to block 114 after incrementing the channel number N at block 119. If the program determines at block 132 that neither of the signals 28 are active, the program simply returns to block 114 after an increment of the channel number N at block 119. At block 114 the decision is made as to whether all of the channels, as for example, both channels in the embodiment illustrated, have been serviced by the program. If the adjustment process has been accomplished on channel 1 then N would equal 2 and the process repeated for channel number 2. If the process has just been completed for channel number 2, block 114 would send the program back to block 110 to again wait for the the period of time during which to again sample signals 28 from remote element 24.

A preferred embodiment of a software program to generate a series of output words for convertor 24 is illustrated the flow charts contained in copending patent application by King-Smith, Remine and Dufresne, entitled, An Output Limited Electrical Stimulator For Biological Tissue, Ser. No. 061745,084, filed June 17, 1985 identified as FN 40895USA1A and assigned to the assignee of the present application, the contents of which are hereby incorporated by reference.

Thus, there has been shown and described a novel electrical stimulator of biological tissue having remote control. It is to be recognized and understood, however, that various changes, modifications and substitution in the form of the details of the present invention may be made by those having skill in the art without departing from the scope of the invention as defined by the following claims.

What is claimed is:

1. An electrical stimulator of biological tissue of a user useful for operable muscle stimulation and for transcutaneous electrical nerve stimulation (TENS) for pain control, comprising:

storage means for storing a plurality of sets of stimulus parameters;

converting means for converting a selected one of said plurality of sets of stimulus parameters to an electrical stimulus output signal which is adapted to be supplied to biological tissue;

remote means for communicating in real time a digital signal from a response from said user to said electrical stimulator to change at least one of said stimulus parameters of said electrical stimulus output signal related to timing, amplitude, pulse duration and repetition rate by switches capable of being controlled by said operator, said digital signal being indicative of a selection of at least one of said plurality of sets of stimulus parameters; and control means operatively coupled to said storage means, said converting means and said remote means, said control means for selecting and coupling, based upon said digital signal from said remote means, one of said plurality of sets of stimulus parameters from said storage means to said converting means, for varying the value of at least one of said stimulus parameters of said one of said plurality of sets of stimulus parameters, said selecting; whereby said electrical stimulator can be used to supply trigger information when said electrical stimulator is providing operable muscle stimulation and for parameter value control when said electrical stimulator is providing TENS.

* * * * *